United States Patent [19]
Frings et al.

[11] 4,012,196
[45] Mar. 15, 1977

[54] COLORIMETRIC METHOD FOR DETERMINING TOTAL LIPIDS IN HUMAN FLUIDS

[75] Inventors: Christopher S. Frings; Ted W. Fendley, both of Birmingham, Ala.; Ralph T. Dunn, Tampa, Fla.

[73] Assignee: Damon Corporation, Needham Heights, Mass.

[22] Filed: May 19, 1975

[21] Appl. No.: 578,726

Related U.S. Application Data

[63] Continuation of Ser. No. 372,267, June 21, 1973, abandoned.

[52] U.S. Cl. .............................. 23/230 B; 252/408
[51] Int. Cl.² .................. G01N 33/16; G01N 21/02
[58] Field of Search .................. 23/230 B; 252/408

[56] References Cited

OTHER PUBLICATIONS

Frings & Dunn, Am. J. Clin. Path., v. 53, pp. 89–91 (1970).
Frings et al., Clin. Chem., v. 18, pp. 673–674 (1972).
Ratliff et al., Advances in Automated Analysis, vol. 1, pp. 101–107 (1972).

Primary Examiner—Morris O. Wolk
Assistant Examiner—Timothy W. Hagan
Attorney, Agent, or Firm—Kenway & Jenney

[57] ABSTRACT

Phospho-vanillin reagent suitable for reaction with a mixture of sulfuric acid and an animal fluid containing at least 1 mg/ml lipids to determine total lipid concentration in the animal fluid comprising an aqueous solution containing vanillin and phosphoric acid having a vanillin to phosphoric acid mole ratio between $1.12 \times 10^{-3}$ and $2.08 \times 10^{-3}$. A sample of the animal fluid is mixed with concentrated sulfuric acid in a container, incubated, and the phospho-vanillin reagent is added to the mixture in the same container to form a chromogen. The light absorbance of the chromogen is measured and the total lipid concentration is determined in accordance with Beer's law from a standard curve relating total lipid concentration as a function of light absorbance by the chromogen.

8 Claims, No Drawings

COLORIMETRIC METHOD FOR DETERMINING TOTAL LIPIDS IN HUMAN FLUIDS

This is a continuation of application Ser. No. 372,267, filed June 21, 1973, now abandoned.

BACKGROUND OF THE INVENTION

This invention relates to a method for determining the concentration of total lipids in animal fluids by a colorimetric method based upon the use of a phospho-vanillin reagent.

Presently, it is believed that abnormal serum lipid concentrations are associated with diseases of the heart such as atherosclerosis. The serum lipids such as cholesterol, phospho-lipids and triglycerides are present in the blood stream both alone and in combination with proteins in the form of lipoproteins. In current analytical practice, the test for total lipid concentration functions as a screening test in that when the concentration is found to be abnormally high, subsequent tests for specific lipids are performed to determine their concentrations in the serum. A common method for determining total lipid concentration involves reacting a serum sample first with sulfuric acid and then with a phospho-vanillin reagent to form a chromogen, the light absorbance of which is measured. The concentration then is determined in accordance with Beer's law from a standard curve relating lipid concentration as a function of light absorbance of the chromogen.

One procedure for carrying out a test for total lipids based upon the phospho-vanillin reagent is described by one of us in the American Journal of Clinical Pathology, Vol. 53, Pages 89–91 (1970). In this procedure, 2 ml. of concentrated sulfuric acid is mixed with a 0.10 ml. of blood serum and heated for about 10 minutes. A 0.10 ml. aliquot of the mixture then is transferred to a second container and 5.0 ml. of a phospho-vanillin reagent is added thereto, mixed and heated for about 15 minutes at 37° C. The mole ratio of vanillin to phosphoric acid in the phospho-vanillin reagent is less than $1.12 \times 10^{-3}$. The light absorbance of the test sample is measured at 540 mu. and the concentration determined from a standard curve. The phospho-vanillin reagent employed is prepared by admixing 800 ml. concentrated phosphoric acid and 200 ml. of a 0.6% (W/V) aqueous vanillin solution.

This procedure as well as other present procedures employing a phospho-vanillin reagent have a number of disadvantages which have limited their use. The prime disadvantage is that these tests require the transfer of a specific volume of the sulfuric acid-serum mixture to a second container prior to adding the phospho-vanillin reagent. This transfer introduces inaccuracies in the test since there will be inaccuracies in the liquid volume measured. The required transfer step also renders their test procedures undesirable for use in automatic testing apparatus wherein serum samples are mixed with reagents and treated on a continuous basis. Furthermore the above-described procedure follows Beer's law only up to a lipid concentration of about 1000 mg/dl and requires a relatively large volume of serum sample of at least 0.10 ml.

It would be highly desirable to provide a test procedure for measuring total lipid concentration in micro quantities of serum which eliminates the use of the present sample transfer procedure since such a procedure would be linear to higher lipid concentrations than present procedures and could be adapted easily for use in automated analysis processes.

SUMMARY OF THE INVENTION

The present invention is based upon the discovery that a test for lipids in animal fluids, including blood serum, involving the sequential reaction of a fluid sample with sulfuric acid and a phospho-vanillin reagent can be accomplished without transferring a specific volume of animal fluid-sulfuric acid sample to a second container by employing a phospho-vanillin reagent having a higher vanillin concentration and a lower phosphoric acid concentration than the reagents presently employed. In accordance with this invention, a test sample of the animal fluid is reacted first with concentrated sulfuric acid, heated in a boiling water bath for at least about 8 minutes and thereafter admixed in the same container with a phospho-vanillin aqueous reagent having a mole ratio of vanillin to phosphoric acid between $1.12 \times 10^{-3}$ and $2.08 \times 10^{-3}$. The mole ratio of phosphoric acid to sulfuric acid is maintained between about 9.5 and 55.5. The resultant mixture is heated at approximately 35° and 39° C for about 13 to 17 minutes, cooled to room temperature and the light absorbance thereof measured at 540 mu.

DESCRIPTION OF SPECIFIC EMBODIMENTS

The process of this invention is carried out by first admixing a sample of human fluid containing at least about 1 mg/ml lipids and concentrated sulfuric acid in a volumetric ratio of the human fluid to sulfuric acid between about 0.2 and about 0.05, and thereafter heating the mixture at a temperature between about 90° and 110° C for a period of time until the sample appears to be digested. Usually, this occurs within about 10 minutes after heating. At the present time, the precise reaction mechanism of the human fluid with sulfuric acid is not known. The mixture then is cooled to about 20° to about 25° C. and thereafter the phospho-vanillin reagent is added to the mixture and the resultant mixture is incubated at a temperature between 35° and 39° C until the reaction mixture turns a pink-red color which usually occurs within about 15 minutes after incubation. The phospho-vanillin reagent is added in amounts such that the mole ratio of phosphoric acid to originally-added sulfuric acid is between about 9.5 and 55.5 and the mole ratio of vanillin to phosphoric acid is between about $1.12 \times 10^{-3}$ and $2.08 \times 10^{-3}$. After incubation, the reaction mixture is cooled to room temperature and within about 30 minutes after cooling, the light absorbance at 540 nm. thereof is measured. The phospho-vanillin reagent reacts with the human fluid-sulfuric acid mixture to form a reaction product which appears as a pink-red color.

In order to account for the light absorbance of the reactants, a blank is prepared by adding to a sample of water having the same volume as the human fluid test sample, the same reagents in the same amounts as are added to the test sample and treating the blank sample in the same manner as the test sample. The light absorbance of the blank sample then is measured at the same light frequency and this value is substracted from that obtained for the test sample prior to determining the actual concentration of the total lipids from the standard curve which relates light absorbance of the chromogen to lipid concentration. The use of the blanking procedure permits obtaining a light absorbance value for the chromogen without interference by excess reactants that may be present in the reagents.

The phospho-vanillin reagent of this invention is prepared conveniently by mixing between 250 and 400 ml. of a 0.6 vol. % vanillin aqueous solution, 450 to 700 ml. of 14.7 M phosphoric acid and if necessary add sufficient water to bring the total volume to 1 liters. During addition of the phosphoric acid to the vanillin reagent the mixture is constantly stirred. The resultant phospho-vanillin reagent contains between $1.12 \times 10^{-3}$ and $2.08 \times 10^{-3}$ moles vanillin per mole or phosphoric acid.

Suitable human fluids that can be tested in accordance with the invention include blood serum, bile fluids, ascites fluid and abdominal fluid. Furthermore, the method is useful as a diagnostic procedure for animal fluids in general as well as human fluids specifically.

The following examples illustrate the present invention and are not intended to limit the same.

EXAMPLE I

A phospho-vanillin reagent was prepared by dissolving 6 grams vanillin in water in a 1 liter flask and diluting to volume with water. 350 ml. of this vanillin reagent was admixed with 50 ml. of water in a 2 liter flask. Thereafter, 600 ml. of concentrated phosphoric acid, specific gravity 1.7, was added to the vanillin reagent with constant stirring. The mole ratio of vanillin to phosphoric acid in the reagent is $1.56 \times 10^{-3}$.

A sample of blood serum was tested as follows: 20 ul. of water and 20 ul. of serum were added each to separate 19 mm. cuvets. Concentrated sulfuric acid, 0.20 ml., was added to each cuvet and mixed in a vortex type mixture. Both cuvets were placed in boiling water for 10 minutes and cooled in water at 25° C for about 5 minutes. Thereafter 10.0 ml. of the phospho-vanillin reagent was added to each cuvet, during which the reagents were mixed on a vortex-type mixer. The samples then were incubated at 37° C in a water bath for 15 minutes, cooled for about 5 minutes to room temperature and then within 30 minutes after cooling, the light absorbance of each sample was measured at 540 nm. on a "Spectronic 70" spectrophotometer.

It was found that the procedure of this example, produced results which follows Beer's law to a lipid concentration of 1250 mg/dl. In addition, no interference with the results was observed when hemoglobin was added to the test sample in amounts up to 1240 mg/dl or when bilirubin was added to the test sample in amounts up to 20 mg/dl.

Since as little as 20 ul. of serum is needed to contact the test, the test is suitable for pediatric patients. In addition, since no pipetting is needed, the test is suitable in present automatic analysis techniques.

We claim:

1. A process for determining total lipid concentration in an animal fluid containing at least 1 mg. lipids per ml. which comprises:
    a. reacting a sample of the animal fluid with sulfuric acid in a container;
    b. subsequently adding directly to the animal fluid-sulfuric acid reaction product in said container, a phospho-vanillin reagent comprising—
        an aqueous solution of vanillin and phosphoric acid having a mole ratio of vanillin to phosphoric acid between $1.12 \times 10^{-3}$ and $2.08 \times 10^{-3}$ to form a chromogen without transferring a specific volume of the sulfuric acid-animal fluid mixture to a second container prior to adding the phospho-vanillin reagent, the mole ratio of phosphoric acid to sulfuric acid added to the animal fluid being between 9.5 and 55.5; and,
    c. measuring the light absorbence of said chromogen, the concentration of total lipids being determined from the measurement of light absorbence of said chromogen,
said mole ratio of vanillin to phosphoric acid and said mole ratio of phosphoric acid to sulfuric acid enabling the addition of the phospho-vanillin reagent directly to the animal fluid-sulfuric acid reaction product and eliminating the necessity of transferring a specific volume of sulfuric acid-animal fluid mixture to a second container prior to adding the phospho-vanillin reagent.

2. The process of claim 1 wherein the animal fluid is blood serum.

3. The process of claim 1 wherein the animal fluid is human blood serum.

4. The process as set forth in claim 3 wherein the blood serum is mixed with sulfuric acid in the container and the mixture is incubated prior to the addition of the phospho-vanillin reagent.

5. The process as set forth in claim 4 further characterized in that the addition of the phospho-vanillin reagent directly to the blood serum-sulfuric acid reaction product enables lipid concentration in excess of 1000 mg/dl to be determined.

6. The process as set forth in claim 4 further characterized in that the addition of the phospho-vanillin reagent directly to the blood serum-sulfuric acid reaction product enables the total lipid concentration to be determined in blood serum samples having a volume less than 0.10 ml.

7. The process as set forth in claim 5 further characterized in that the addition of the phospho-vanillin reagent directly to the blood serum-sulfuric acid reaction product enables the total lipid concentration to be determined in blood serum samples having a volume less than 0.10 ml.

8. The process as set forth in claim 4 wherein the light absorbance is measured at 540 m$\mu$.

* * * * *